United States Patent [19]

Ludwick

[11] Patent Number: 5,662,665

[45] Date of Patent: Sep. 2, 1997

[54] SUTURE NEEDLE HOLDING SURGICAL INSTRUMENT

[76] Inventor: Jack Rydel Ludwick, 201 Rocky Pt. Rd., Palos Verdes Estates, Calif. 90274

[21] Appl. No.: 471,405

[22] Filed: Jun. 6, 1995

[51] Int. Cl.$^6$ .................................................. A61B 17/00
[52] U.S. Cl. ........................ 606/147; 606/148; 606/151; 606/207; 81/300; 81/421; 81/424.5
[58] Field of Search ........................ 606/147, 148, 606/145, 144, 151, 205, 207, 208, 139; 81/300, 418, 421, 424.5, 426.5

[56] References Cited

U.S. PATENT DOCUMENTS

| | | | |
|---|---|---|---|
| 348,537 | 8/1886 | Stohlmann | 606/147 |
| 3,842,840 | 10/1974 | Schweizer | 606/145 |
| 4,961,742 | 10/1990 | Torre | 606/147 |
| 5,133,737 | 7/1992 | Grismer | 606/205 |
| 5,242,458 | 9/1993 | Bendel et al. | 606/147 |
| 5,389,103 | 2/1995 | Melzer et al. | 606/147 |

*Primary Examiner*—Jeffrey A. Schmidt

[57] ABSTRACT

A surgical instrument for holding a suture needle is disclosed. The instrument is of scissors configuration with elongated arms having finger loops at one end and jaws at the other end to grasp a suture needle. This improved instrument has specialized jaws containing a transverse channel that securely holds a suture needle at a right angle to the axis of the needle holder. The width of the transverse channel automatically adjusts to the size of the suture needle as it is being placed in the needle holder. This improved configuration significantly reduces the long standing problem of suture needle twisting or rotation in the needle holder jaws as the surgeon passes the needle through tissue.

6 Claims, 5 Drawing Sheets

SUTURE NEEDLE HOLDING SURGICAL INSTRUMENT

FIELD OF THE INVENTION

The subject invention relates generally to surgical instruments, and more particularly to a holding instrument, for a suture needle.

BACKGROUND OF THE INVENTION

It is common surgical practice for a physician to join various tissues by passing a needle with attached suture through the tissue. The suture is then tied to approximate the tissues. There are several prior art plier-like instruments available for gripping and holding suture needles. A conventional instrument for passing the needle through the tissues is a needle holder which usually has a pair of movable, opposed jaws connected to a pair of handles. The handles in turn have a scissor configuration with a locking ratchet mechanism to maintain gripping pressure on the needle held in the jaws of the needle holder.

Needle holder jaws commonly have a tungsten carbide, serrated surface in a diamond or cross-hatched pattern to enhance the firmness with which the needle is grasped. The ratchet mechanism between the scissor handles is locked as the handles close thereby maintaining firm gripping pressure on the suture needle. Despite this construction, needles are frequently subject to twisting or slipping in the jaws of needle holders as they pass through tissue. Normally the surgeon releases the ratchet mechanism only after the needle has safely passed through the tissue. If during passage of the suture needle, the needle twists or moves off the desired axis of travel, tissue may be torn, needles may be lost, and the operation time prolonged. Twisting movement of a suture needle in the needle holder jaw is a frustrating and dangerous problem which has not been solved by prior art.

SUMMARY OF THE INVENTION

It is an object of the present invention to provide a surgical needle holder that securely holds a suture needle as it passes through tissue. It is an object to minimize slipping or twisting of the suture needle in the jaws of the needle holder as the needle passes through tissue. Prior art has not solved the long standing problem of unwanted motion of the suture needle while still in the grasp of the needle holder.

The present invention consists of a surgical needle holder with finger-loop handles which have a ratchet locking mechanism connected to two elongated scissoring members that in turn define specialized opposing jaws that hold the suture needle. In this improved invention the jaws of the needle holder have a distal transverse channel that securely hold the suture needle at a right angle as it passes through tissue. The transverse channel in the needle holder jaw is of adjustable width to accomodate suture needles of different size. The width is easily adjusted during a surgical procedure, so that needles of various width can be accommodated without changing needle holders. In addition, the floor of the transverse channel is of ribbed design to mate with the surface of the suture needle.

Both jaws of the needle holder have a mirror-imaged adjustable transverse channel design, so there is no top or bottom orientation required for the needle holder. The needle holding transverse channel adjusts to the diameter of the needle by a biasing sliding member of the needle holder jaw. This design allows quick placement of the needle in the holder and maintains proper, secure alignment of the needle at right angles to the jaws of the needle holder.

DETAILED DESCRIPTION OF THE INVENTION

Figure 1:
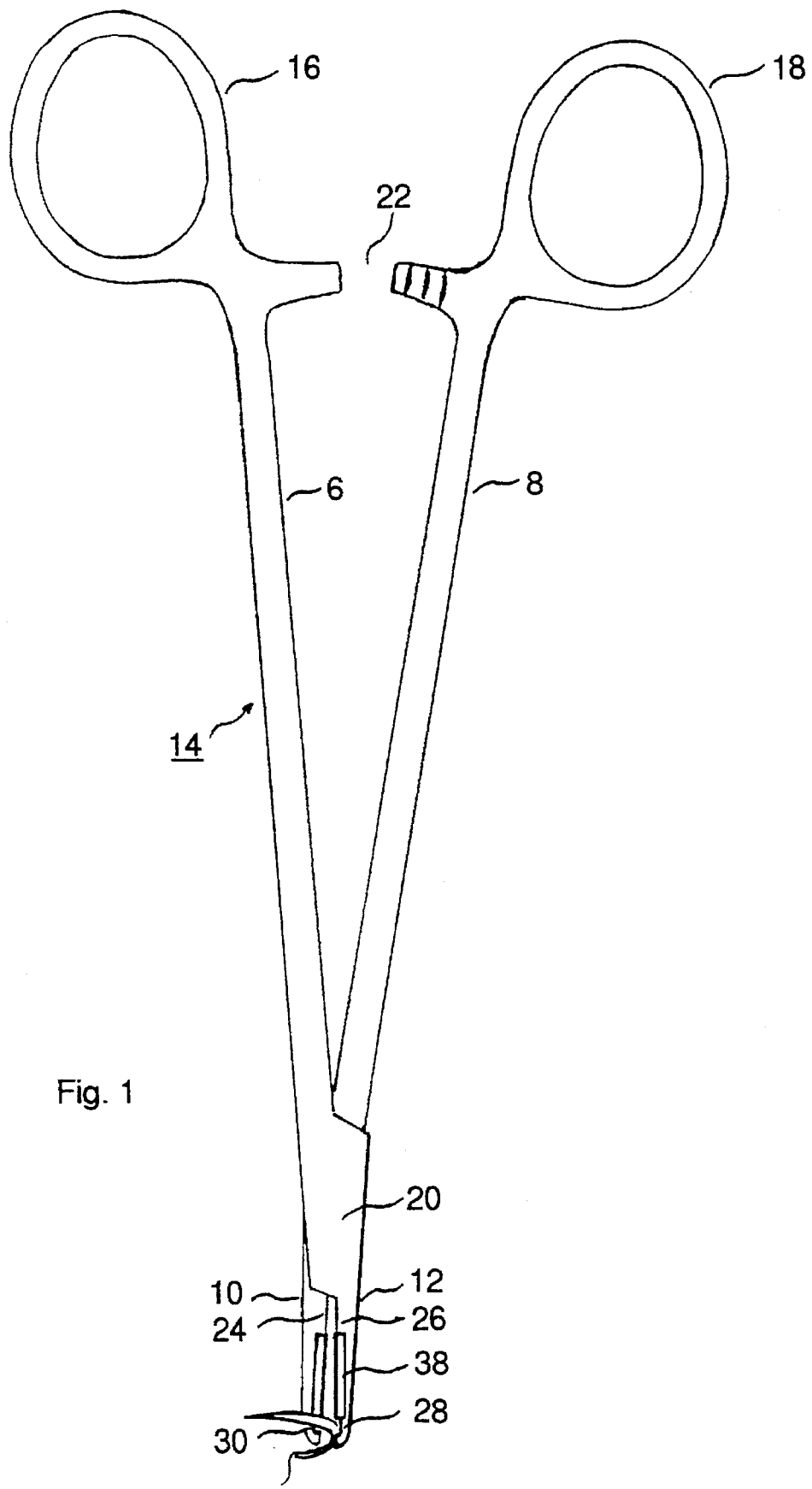
FIG. 1 is a side view of the subject needle holder showing a suture needle positioned in the specialized transverse channels 28, 30.

FIG. 1 shows the needle holding instrument of the present invention with the embodiment of a specialized distal transverse channel in the jaws of the needle holder to securely grasp a suture needle. The needle holder 14 is preferably constructed of surgical stainless steel.

At the proximal end finger loops 16 and 18 are of a size to accept thumb or finger within the loop. The finger loops are in turn connected to elongated arms 6 and 8.

Protruding at or near the junction of the finger loops 16, 18 and the elongated arms 6, 8 is a conventional locking ratchet mechanism 22. The ratchet lock 22 consists of two short members, at the junction of the finger loops with the elongated arms, and perpendicular to the arms of the needle holder. These members have matching notches on their opposing surfaces which engage one another, locking, as the finger loops are brought together. Such locking ratchet mechanism is well known to the art.

The elongated arms are of equal length and terminate at a pivot joint 20. Conventionally the pivot joint 20 is constructed such that the elongated arms of the needle holder terminate in a short, flat, widended area. Any pivot method can be used, traditionally, the flat area of one arm passes thru a matched opening in the other arm with both being united to one another by a pin passing through the center of the flat zone. Both arms pivot about this pin establishing the scissors action of the needle holder. This configuration allows the distal jaws to be centered on one another rather than offset as is the case with the usual cutting scissors. The elongated arms for open surface surgery are shorter than those in the case of laparoscopic surgery.

The finger loops and elongated arms allow the surgeon to grasp the instrument and apply pressure to close it. Once closed, the ratchet mechanism locks to maintain the closed position. The ratchet mechanism is opened by the surgeon applying opposing pressure to the finger loops. The pivot joint allows for ease of opening and closing the jaws 10 and 12. The needle holder jaws taper in both width and heigth to a terminal, rounded point. This pointed tip allows for good directional placement and visualization of needle position by the surgeon using the instrument.

Figure 2:
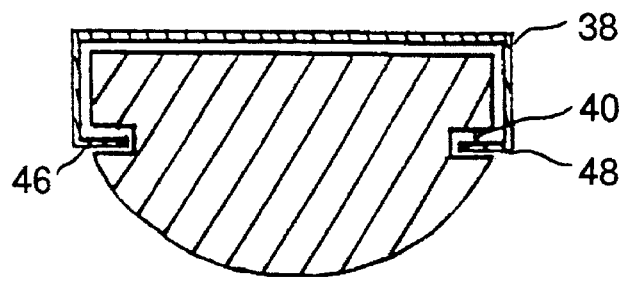
FIG. 2 is a cross section of the needle holder jaw showing the longitudinal grooves in which the top sliding member 38 moves.
Figure 3:
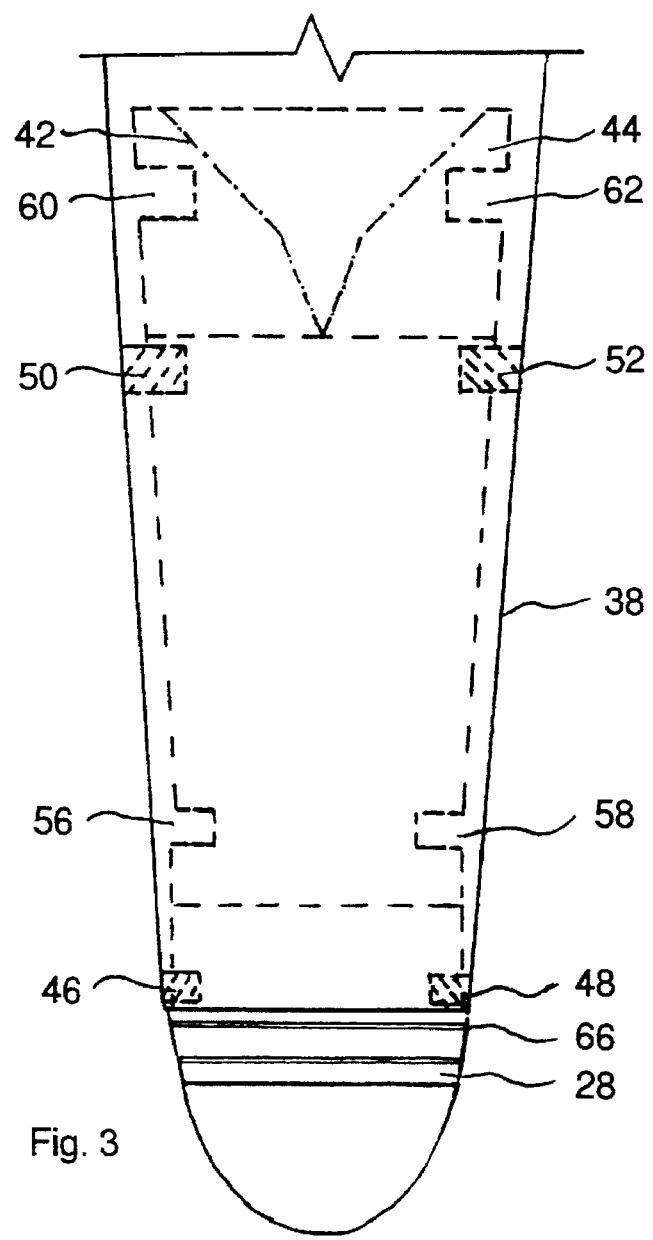
FIG. 3 is a top view of the needle holder jaw showing the sliding member 38, distal transverse channel 28 and proximal spring compartment 44.

The needle holding jaws with opposed surfaces 24 and 26 contain specialized transverse channels 28 and 30, shown in greater detail in FIGS. 2–4. The width of the transverse channel varies by means of sliding member 38. Construction of the needle holder jaws is of surgical stainless steel. Alternatively the jaws may be made of high impact plastic to afford a disposable nature to this functional section of the surgical instrument. This would allow for cleaning and sterilizing the reusable parts and for discarding the jaws in the case of fatiqued surfaces that no longer securely grasp the suture needle.

FIG. 2 is a section across one needle holder jaw. The sliding member 38 is of surgical stainless steel or tungsten carbide construction. All stainless steel or tungsten carbide parts can be sterilized and re-used. Alternatively, it is made of high impact plastic for disposable application. The sliding member 38 is rectangular in shape and comprises a major portion of the needle holder jaw. The surface of the sliding member is preferably finished in a serrated or cross-hatched pattern. This provides an alternative grasping surface for a needle or suture (the latter being the case when the needle holder is used to tie the suture). The sliding member moves back and forth as constrained by longitudinal grooves 40. The longitudinal grooves are provided in the side of the needle holder jaw to a depth to securely hold tabs 46 and 48. Two or more tabs 46 and 48 which are part of the rolled over edge of the sliding member maintain the sliding member in position on the needle holder jaw. The motion of the sliding member back and forth in the longitudinal grooves 40 allows for variation in the width of the transverse channel described in FIG. 1 and 5–7.

FIG. 3 is a detailed top view of the needle holder jaw. In the pictured embodiment the sliding member 38 moves in the longitudinal grooves 40 by means of four tabs 46, 48, 50, 52. These tabs are introduced and removed through vertical openings 56, 58, 60, 62, in the side of the needle holder jaw to allow the tabs to enter the longitudinal groove 40. Once seated in the groove the sliding member is held in position by a biasing spring 42, such as a leaf spring, in proximal compartment 44. The leaf spring is held in place in the compartment by one fitting the ends into spring locating grooves in the end wall of the compartment. This prevents the spring from inadvertant dislocation from the compartment. The spring 42 exerts moderate forward pressure on the sliding member 38. The amount of forward pressure is such that a suture needle can be easily placed into transverse channel 28 and the sliding member 38 move to accomodate the size of the needle.

Once the needle is in the transverse channel and the needle holder jaws are closed, the sliding member is firmly held in place against the needle both by the biasing member and by the closing force of opposing jaws. In a preferred embodiment, the suture needle is further securely held in position in the transverse channel 28 by virtue of one or more transverse ribs or elevations 66 in the floor of the transverse channel. These ribs mate with corresponding longitudinal grooves in the surface of the suture needle as will be described in more detail with referance to FIGS. 4–7. The surfaces of the needle holder jaw not involved with the transverse channel are preferably of a serrated or cross hatched design to allow for alternate needle grasping capability.

Figure 4A:
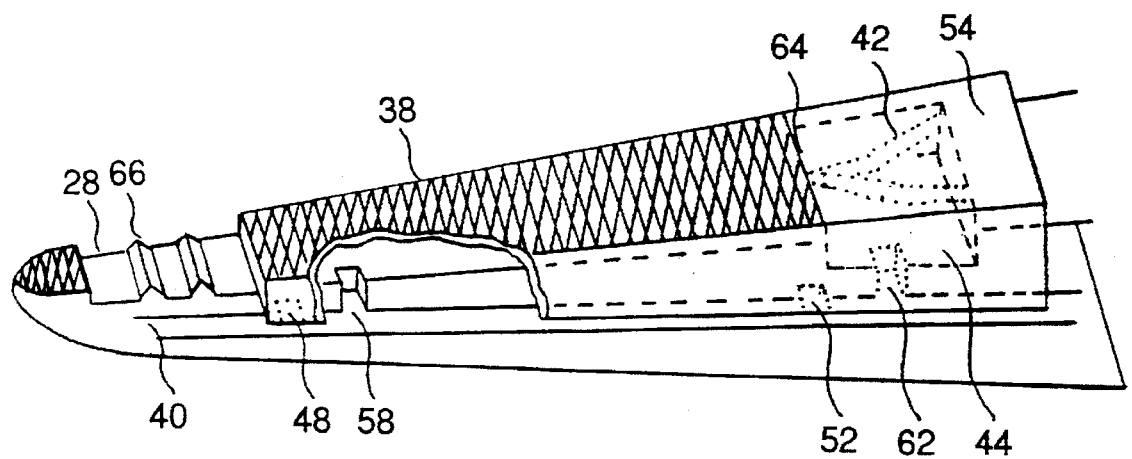
FIG. 4a is an oblique view of the needle holder jaw showing the transverse channel 28 with varying width maintained by sliding member 38.

FIG. 4a is an oblique view of a preferred embodiment of the needle holder jaw. The sliding member 38 is positioned such that in a resting state there is a 1.5 mm opening at the front of the transverse channel 28. This allows ease of placement of a suture needle as it seats directly in this opening. If the diameter of the needle is larger than 1.5 mm the sliding member moves back to allow full seating of the larger diameter. As the sliding member moves back there is compression of the spring 42 in compartment 44.

The sliding member 38 can be removed and replaced in position by compressing the spring 42 with maximum pressure pushing it back until tabs 46, 48, 50, 52 meet four matching vertical openings 56, 58, 60, 62, in the upper edge of the longitudinal grooves 40. The motion is to push the sliding member back as far as possible so that the tabs engage the vertical openings and the sliding member can be lifted up and free. The reverse motion allows replacement of the sliding member in the needle holder jaw.

The opening of the spring compartment 44 is covered by an extension 54 of the sliding member 38. In addition, there is an inferior small projection 64 of the sliding member 38 which is in contact with and holding the spring 42 in functional position.

Figure 4B:
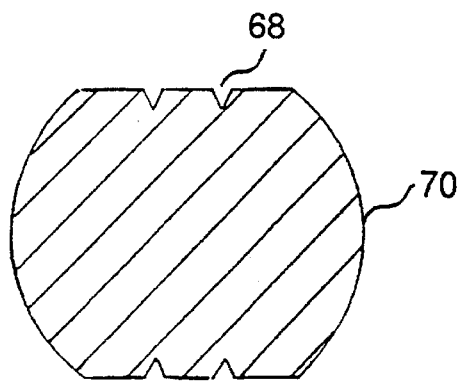
FIG. 4b is a cross section of the preferred suture needle.

The depth of the transverse channel 28 is approximately 1 mm. In the floor of the transverse channel 28 there are one or more transverse triangular ridges or elevations 66 which are designed to engage longitudinal grooves 68 on the surface of the suture needle 70. The preferred cross-section of the suture needle is depicted in FIG. 4b. This configuration allows the suture needle 70 to seat in the transverse channel 28 and maintain its position at a right angle to the axis of the needle holder jaws. In surgical applications the needle must maintain its location in the needle holder as it passes through tissue. Any motion of the suture-needle from the desired right angle results in lost time or a lost needle in addition to the potential damage of tissue by unwanted needle motion.

Figure 5:
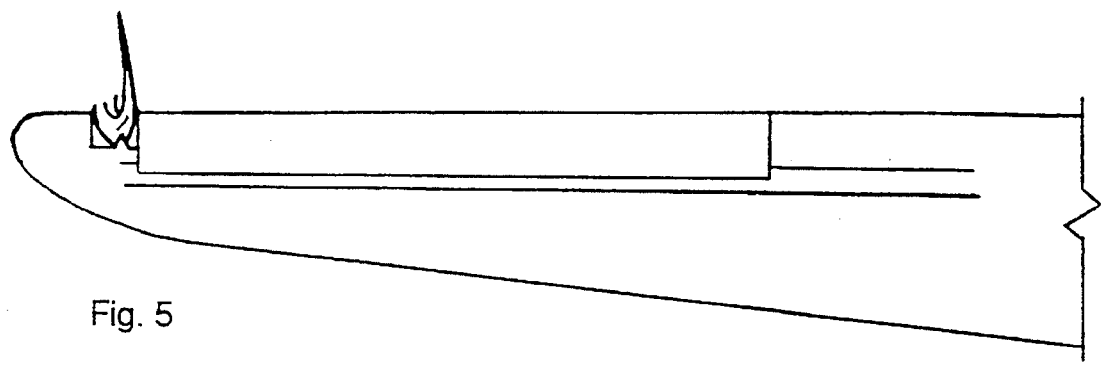
FIG. 5 is a side view of the transverse channel with a small suture needle.
Figure 6:
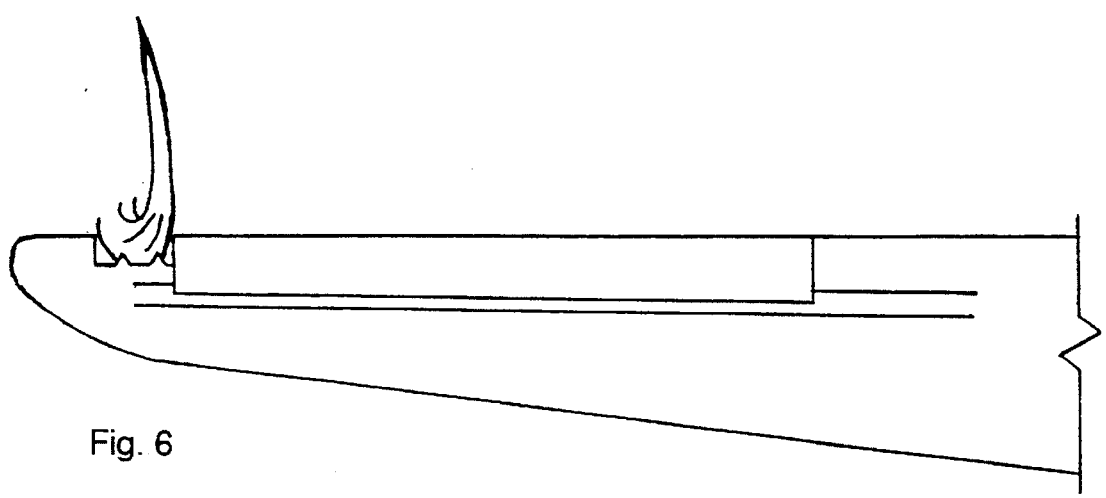
FIG. 6 is a side view of the transverse channel with a large suture needle.

FIG. 5 shows the side view of the needle holder jaw with a suture needle 70 in position in the transverse channel 28. This needle is fairly small resulting in opening of the sliding member 38 only a minimal amount. FIG. 6 depicts a larger needle in the transverse channel 28 resulting in an increased opening of the sliding member 38. Note that in both FIG. 5 and 6 there is mating of the transverse ridges 66 in channel 28 with the grooves 68 in the needle 70 surface. This provides a secure grasp of the needle 70. The firm positioning of the suture needle 70 is further enhanced by the closed approximation of the opposed needle holder jaws 10, 12 that aid in maintaining the sliding member 38 against the seated needle 70. There are three separate constraints being applied simutaneously to the suture needle to maintain its position in the transverse channel 28. First, the transverse ridges 66 in the channel are mating with the grooves 68 in the surface of the suture needle 70 to inhibit lateral movement. Second, the forward pressure of biasing by the sliding member 38 on the needle maintains the needle in the transverse channel 28. The third force is the pressure of the closed jaws 10, 12 of the needle holder 14 on each other which is maintained by the locked ratchet mechanism 22. This last force is additive to the first two by maintaining the sliding member 38 firmly against the needle 70 and by keeping the needle 70 seated on the transverse ridges 66 in the transverse channel 28. Generally the needle 70 will seat in the lower jaw as the convex surface of the needle is pushed into place in the needle holder jaw. Both jaws 10, 12 are the same, so the upper transverse channel 30 facing the concave surface of the needle will also be utilized if the needle is thick enough to activite the sliding member 38. With a suture needle 70 properly seated the opposing surfaces 24 and 26 of the needle holder jaws will be in contact.

Alternatively, depending on the size of the needle holder 14 and the suture needle 70 being used, only one jaw of the needle holder 14 might have the specialized transverse channel 28 herein described. The opposing needle holder jaw surface 24, 26 would be of flat, conventional design without a transverse channel 28. This may require a top/bottom designation to the needle holder jaws 10, 12 for ease of use. This can be done by marking the needle holder handles or color coding the transverse channel 28 for quick orientation. In addition, it is possible that in small needle holder, applications that there would not be a sliding member 38 in the design. This would require the width of the transverse channel 28 in the needle holder jaw to be of a fixed dimension. Thusly, in this situation suture needles 70 of only one size would fit into the transverse channel 28. This configuration may be desirable in needle holders for fine vascular or ophthalmologic surgery.

Figure 7:
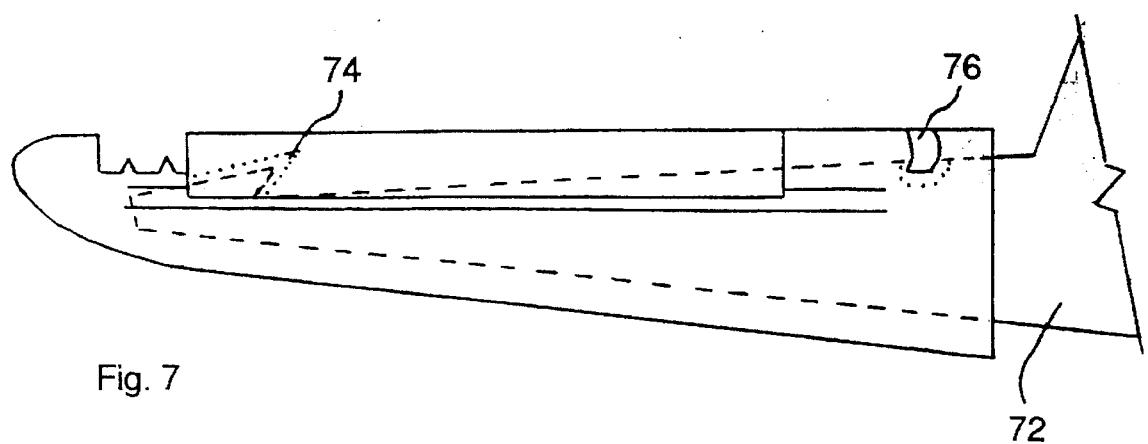
FIG. 7 is a side view of the needle holder jaw showing the removable/disposable feature for the entire jaw mechanism.

Construction of the improved needle holding instrument is of surgical stainless steel or tungsten carbide. Alternately, the specialized jaws may be constructed of high impact plastic and designed to be disposible and replaceable, as a unit on the needle holder. FIG. 7 shows a side view of a disposable configuration in which the entire jaw mechanism can be removed from the needle holder. There is a central longitudinal support 72 extending forward from the needle holder pivot joint 20. The jaw mechanism with specialized transverse channel 28 fits over the longitudinal support 72 and snaps in place. This is done by means of a tongue and groove joint 74 at the distal portion and a snap-lock 76 at the proximal end of the needle holder jaw. The tongue and groove joint 74 has an angled projection of metal from the support 68 which fits into an angled groove in the inner surface of the disposable jaw insert. The snap-lock mechanism 76 consists of a transverse spring on the jaw, the ends of which fit into corresponding grooves in the longitudinal support 72 as the jaw is pressed into position. The motion to place the jaw insert is to engage the distal tongue and groove joint 74 first then press the rear of the jaw down to allow the spring ends to snap into place in the grooves in the longitudinal support 72. To remove the disposable needle holder jaw insert, the proximal snap-lock joint 76 must be disengaged on one side with an instrument then the insert can be lifted up and off the longituidal support.

The above described embodiment of the invention is the preferred form. However, it is understood that changes in the design construction may be made without departing from that which is herein claimed. For example, the transverse channel 28 may be placed at an angle other than a right angle to the axis of the needle holder for certain surgical applications. The needle 70 may be more or less curved, or may be straight. The needle grooves 68 and ridges 66 may be triangular, squared, rounded or eccentric. The spring 42 may be a leaf or coiled spring. The sliding member 38 may provide no tabs, 2 tabs, 4 tabs, or the like. Substitute materials may be used.

I claim:

1. A suture needle holding surgical instrument comprising:

first and second elongated members, each of which form finger loops at a first end and jaws to hold a suture needle at a second end; said first and second elongated members being pivotally mounted in a scissors configuration;

at least one jaw with a specialized transverse channel in an inner jaw surface;

a sliding member; and a biasing member associated with said sliding member and said at least one jaw, for moving said sliding member to adjust the width of said transverse channel in response to the introduction of a suture needle into said transverse channel.

2. An instrument of claim 1 wherein the instrument includes a ratchet locking mechanism for holding the jaws in a pivotally closed position.

3. An instrument of claim 1 wherein said transverse channel includes a floor having at least one transverse ridge for mating with a corresponding groove in a suture needle surface.

4. An instrument of claim 3 wherein both said first and second elongated members have a specialized transverse channel including a floor having at least one transverse ridge in said channel.

5. An instrument of claim 1 wherein inner surfaces of the needle holder jaws not defining said transverse channel are of a serrated configuration.

6. An instrument of claim 1 wherein said sliding member and entire jaw on the end of the first elongate member as well as the entire jaw on the end of the second elongate member are removable.

* * * * *